United States Patent
Alhourani

(10) Patent No.: US 10,231,825 B2
(45) Date of Patent: Mar. 19, 2019

(54) ALTERNATIVE TO RESECTION PROCEDURE USING RAKAN'S ADJUSTABLE SQUINT DEVICE

(71) Applicant: Rakan Elias Jamil Alhourani, Alfuhais (JO)

(72) Inventor: Rakan Elias Jamil Alhourani, Alfuhais (JO)

( * ) Notice: Subject to any disclaimer, the term of this patent is extended or adjusted under 35 U.S.C. 154(b) by 94 days.

(21) Appl. No.: 15/582,628

(22) Filed: Apr. 29, 2017

(65) Prior Publication Data

US 2018/0311073 A1    Nov. 1, 2018

(51) Int. Cl.
*A61F 2/14* (2006.01)
*A61F 9/007* (2006.01)
*A61F 9/00* (2006.01)

(52) U.S. Cl.
CPC .......... *A61F 2/14* (2013.01); *A61F 9/007* (2013.01); *A61F 9/0017* (2013.01); *A61F 9/0026* (2013.01); *A61F 2220/0008* (2013.01)

(58) Field of Classification Search
None
See application file for complete search history.

(56) References Cited

U.S. PATENT DOCUMENTS

| 4,519,392 A * | 5/1985 | Lingua .............. A61B 17/11 606/151 |
| 7,670,361 B2 * | 3/2010 | Nesper ............. A61B 17/688 128/898 |
| 9,155,604 B1 * | 10/2015 | Wright ............. A61F 9/007 |
| 2005/0125015 A1 * | 6/2005 | McNally-Heintzelman ......... A61B 17/08 606/151 |
| 2006/0287720 A1 * | 12/2006 | Tse ................. A61B 17/8061 623/4.1 |

FOREIGN PATENT DOCUMENTS

WO   WO-2010118514 A1 * 10/2010 ............ A61F 2/14

* cited by examiner

*Primary Examiner* — David H Willse
*Assistant Examiner* — Javier G Blanco

(57) ABSTRACT

The present invention is a device that is used in squint surgeries which contains two parts: the first part is fixated to the insertion and the second part is fixated to the muscle/muscle tendon, and the two parts are connected to each other with two threads at both sides, in this device the distance between the two parts can be adjusted; hence the magnitude of muscle resection or recession. Also a new procedure (alternative to resection procedure) is provided; in which we shorten the muscle without resecting it. In addition to the main device, there is a tiny sclera screws that can fixate any device implanted on the sclera.

1 Claim, 18 Drawing Sheets

ALTERNATIVE TO RESECTION PROCEDURE USING RAKAN'S ADJUSTABLE SQUINT DEVICE

CROSS-REFERENCES TO RELATED APPLICATIONS

Not Applicable

STATEMENT REGARDING FEDERALLY SPONSORED RESEARCH OR DEVELOPMENT

Not Applicable

STATEMENT REGARDING PRIOR DISCLOSURES BY THE INVENTOR OR A JOINT INVENTOR

Not Applicable

FIELD OF THE INVENTION

The present invention generally relates to a device that is used in squint surgeries, which by we can adjust the magnitude of extraocular muscle recession or resection in order to achieve the best alignment, and this new device can be used as an alternative to resection procedure in a way that preserves the blood supply through the muscle to the eye. In addition to the main device, Rakan's sclera screws can be used to fixate any device implanted on the sclera.

BACKGROUND OF THE INVENTION

Rakan's adjustable squint device has many applications in squint surgeries, this adjustable device allows us to readjust the length needed for extraocular muscle recession or resection and we can redo the adjustment at any time. Furthermore this device allows us to do an alternative to resection procedure, in this new procedure we shorten the muscle but we don't resect it, so we preserve the blood vessels supplying the eye and we can readjust the length of shortening.

Rakan's sclera screws are tiny screws that can fixate any device implanted on the sclera of the eye instead of using sutures through the sclera.

SUMMARY OF THE INVENTION

The present invention is a squint procedure that is described as alternative to resection procedure, in this new procedure we shorten the muscle but we don't resect it using a special device. This device contains two parts: first part is the fixed part which is fixed over the muscle insertion and second part is the movable part which is attached to the muscle/muscle tendon, the two parts are connected at both sides by two threads that their lengths can be adjusted. In addition to the main device there are tiny sclera screws that can fixate any device implanted on the sclera.

DETAILED DESCRIPTION OF THE INVENTION

Figure 1:
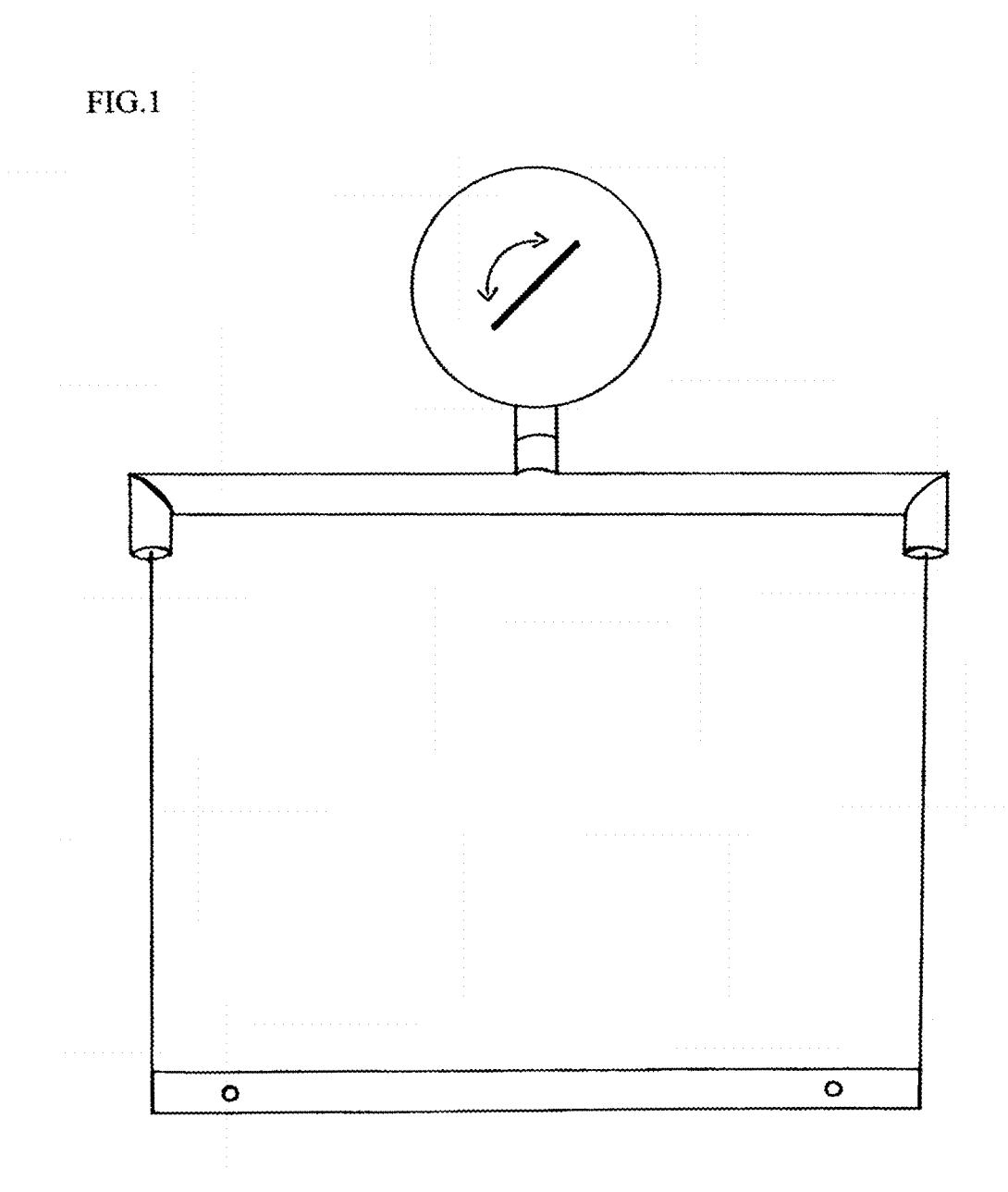
FIG. 1: General view of Rakan's adjustable squint device with two threads connecting the two parts—the curved arrows illustrate the rotatory directions.
Figure 4:
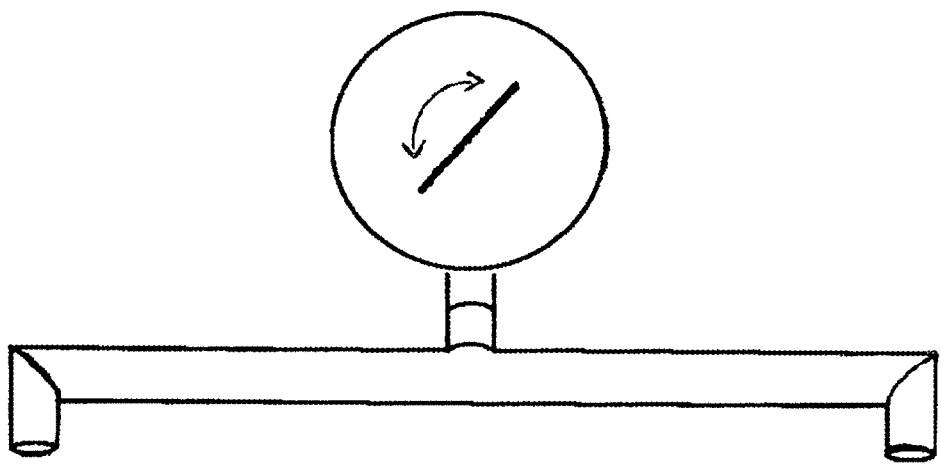
FIG. 4: The first part of Rakan's adjustable squint device: the fixed insertion part.
Figure 12:
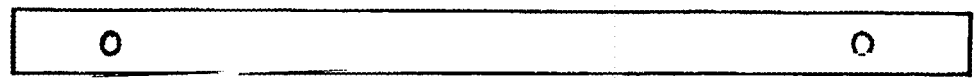
FIG. 12: The second part of Rakan's adjustable squint device: the movable muscle/muscle tendon part—above view.
Figure 15:
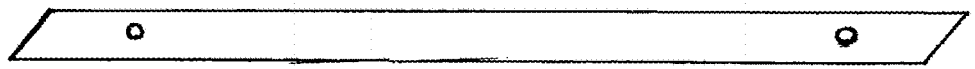
FIG. 15: The second part of Rakan's adjustable squint device: the movable muscle/muscle tendon part—side view from above.
Figure 15:
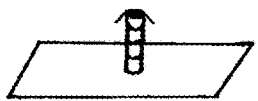
Figure 15:
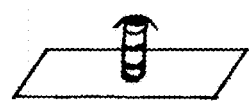

Rakan's adjustable squint device FIG. 1 contains two parts: the first part—fixed insertion part FIG. 4 and the second part—movable muscle/muscle tendon part FIG. 12/FIG. 15, the two parts are connected by two threads at both sides, the length of the threads can be adjusted so we can determine and adjust the distance between the two parts, which means we can readjust the magnitude of recession or resection.

Figure 5:
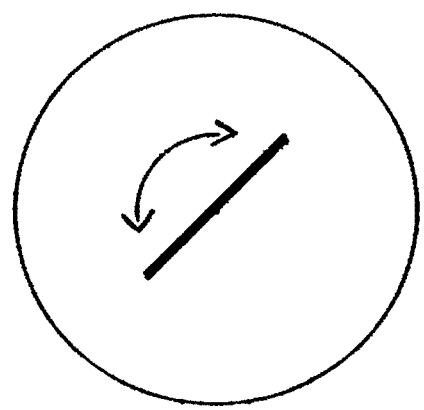
FIG. 5: The adjustable part of the fixed insertion part—the curved arrows illustrate the rotatory directions.
Figure 7:
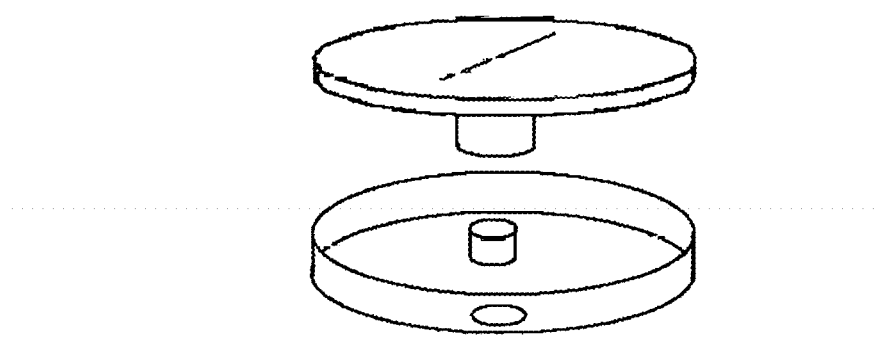
FIG. 7: The adjustable part of the fixed insertion part (the inner rotatory piece is elevated for illustration).
Figure 10:
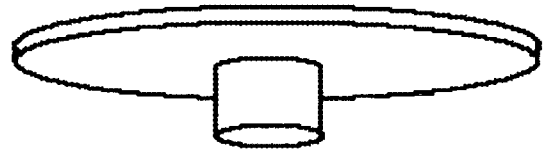
FIG. 10: The inner rotatory piece of the adjustable part—side view from below.
Figure 11:
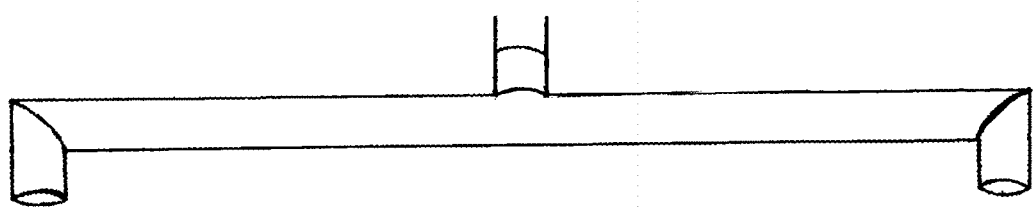
FIG. 11: The tubule system part of the fixed insertion part.

The first part FIG. 4 is the fixed insertion part which is implanted over the insertion of the extraocular muscle at the eye globe, and it contains two parts: the adjustable part/portion FIG. 5 and the tubule system part/portion FIG. 11. The adjustable part FIG. 5/FIG. 7 contains two pieces: the outer fixed piece FIG. 8 and the inner rotatory piece FIG. 9/FIG. 10.

Figure 8:
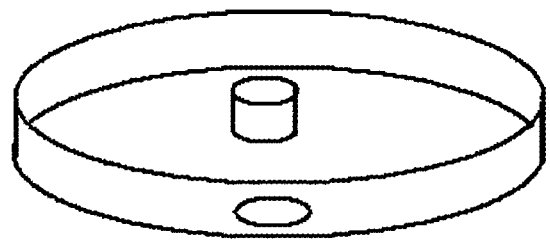
FIG. 8: The outer fixed piece of the adjustable part.

The outer fixed piece FIG. 8 is cylindrical in shape, and fixed non-movable: Its base circular flat surface is closed, its side curved surface is closed except at an opening that connects it with the tubule system part, and its top circular flat surface is open. At the center of the outer fixed piece and inside it, there is a middle cylindrical shaft which is filled.

Figure 6:
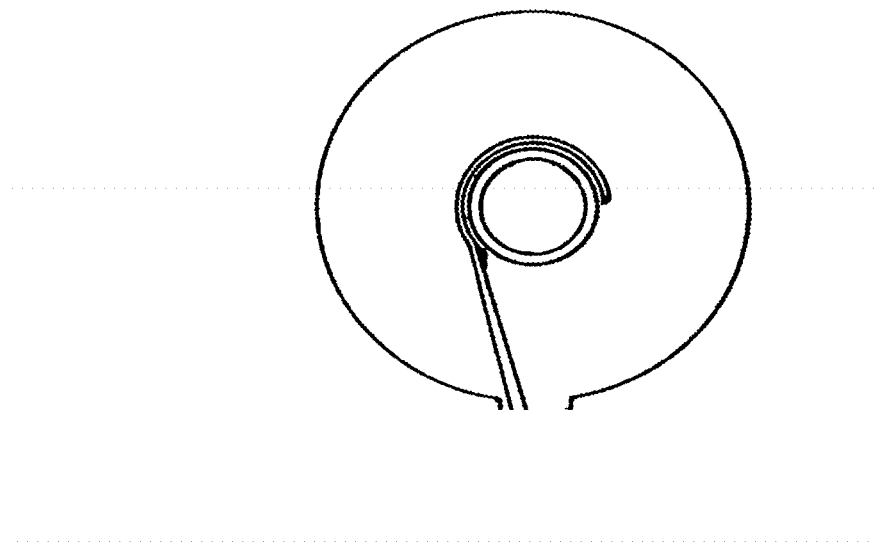
FIG. 6: View for the inside (almost half-deep cut) of the adjustable part of the fixed insertion part—with threads.
Figure 9:
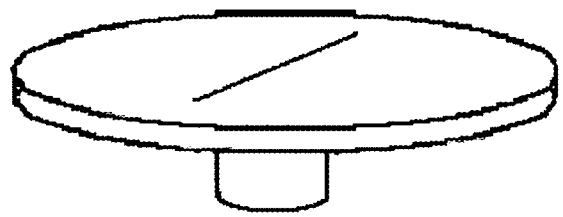
FIG. 9: The inner rotatory piece of the adjustable part—side view from above.

The inner rotatory piece FIG. 9/FIG. 10 is a blunt/filled (not hollow) cylinder with much shorter height than the outer fixed piece: At its top circular surface there is a handle by which we rotate the whole inner piece, and below its base circular surface there is a hollow cylindrical shaft which is situated at the base center; this hollow shaft is open from its base, the hollow shaft's top is closed and connected to the filled cylinder above, and the hollow shaft's curved side surface is closed. The two threads that connect the two parts of Rakan's adjustable squint device are attached to the curved side surface of the hollow shaft (from outside) so when the hollow shaft is rotated, the threads are wrapped around it and eventually shortening or lengthening of the threads between the two parts of Rakan's adjustable squint device. The filled cylindrical shaft of the outer fixed piece settles and fits inside the hollow cylindrical shaft of the inner rotatory piece, so the shaft of the outer piece works as an axis for the rotation of the inner piece's shaft; the inner piece rotates around the shaft of the outer piece, as shown in FIG. 6: the inner circle represents the filled shaft of the outer fixed piece, the middle circle represents the hollow shaft of the inner rotatory piece, the two threads are fixed to and warp around the hollow shaft (of the inner rotatory piece) and then directed to exit out of the outer fixed piece from its side curved surface opening.

The tubule system part of the fixed insertion part FIG. 11 contains tubules that are designed in a special shape that directs the two threads from the adjustable part to the both sides of the muscle insertion (one thread at each side).

Figure 13:
FIG. 13: Two wedges: part of the movable muscle/muscle tendon part—above view.
Figure 13:
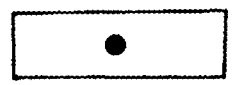
Figure 14:
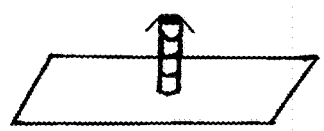
FIG. 14: A muscle/muscle tendon wedge—side view from above.

The movable muscle/muscle tendon part FIG. 12/FIG. 15 contains a shaft that crosses over the muscle or the tendon of the muscle horizontally and wedges FIG. 13/FIG. 14 that cross through the muscle/the tendon and fixate the muscle or the tendon to the shaft.

Figure 2:
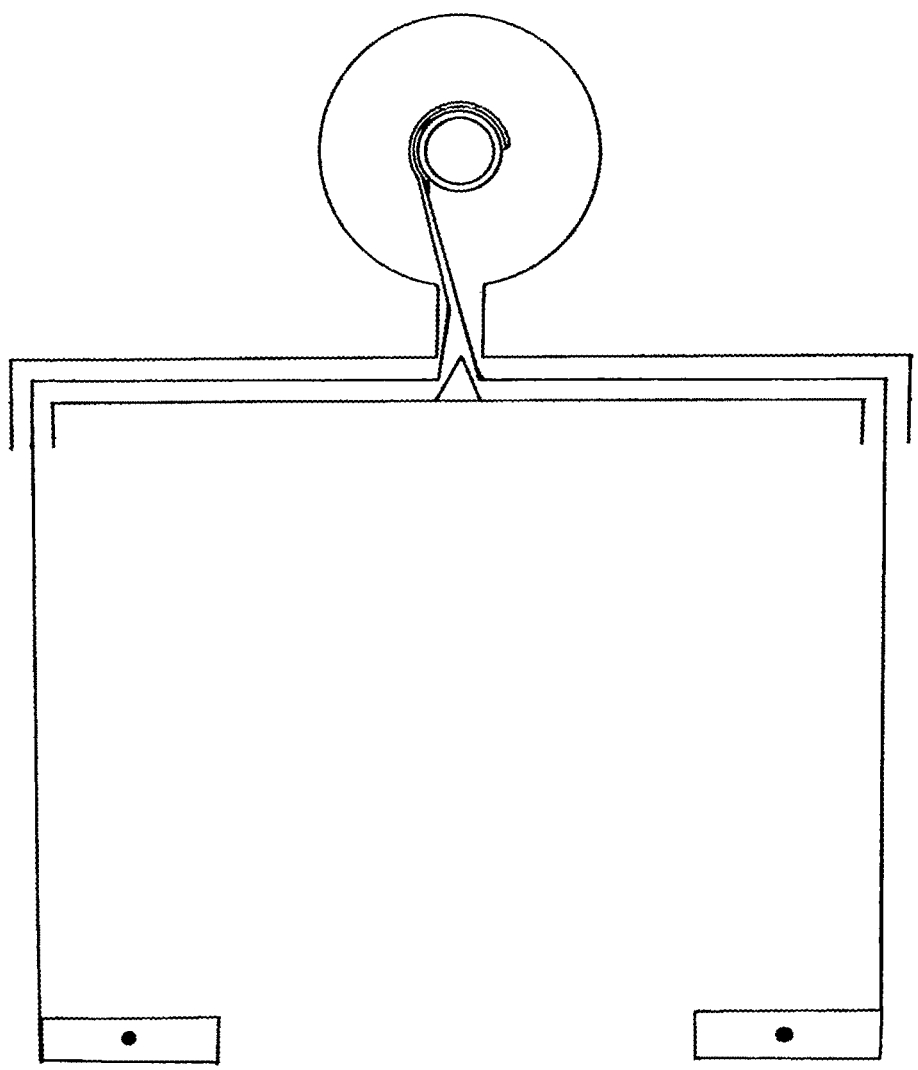
FIG. 2: View for the inside (almost half-deep cut) of Rakan's adjustable squint device—with two threads connecting the two parts.

FIG. 2 which is a view for the inside (almost half-deep cut) of Rakan's adjustable squint device, illustrates the path of the two threads which starts at the hollow shaft of the inner rotatory piece, then they warp around it, and then they exist the adjustable rotatory part to enter the tubule system part, then through the tubule system part the two threads are split and directed in opposite directions (one for each side of the muscle insertion), then the two threads directed out and away from the tubule system part to connect and attach the movable muscle/muscle tendon part.

Figure 3:
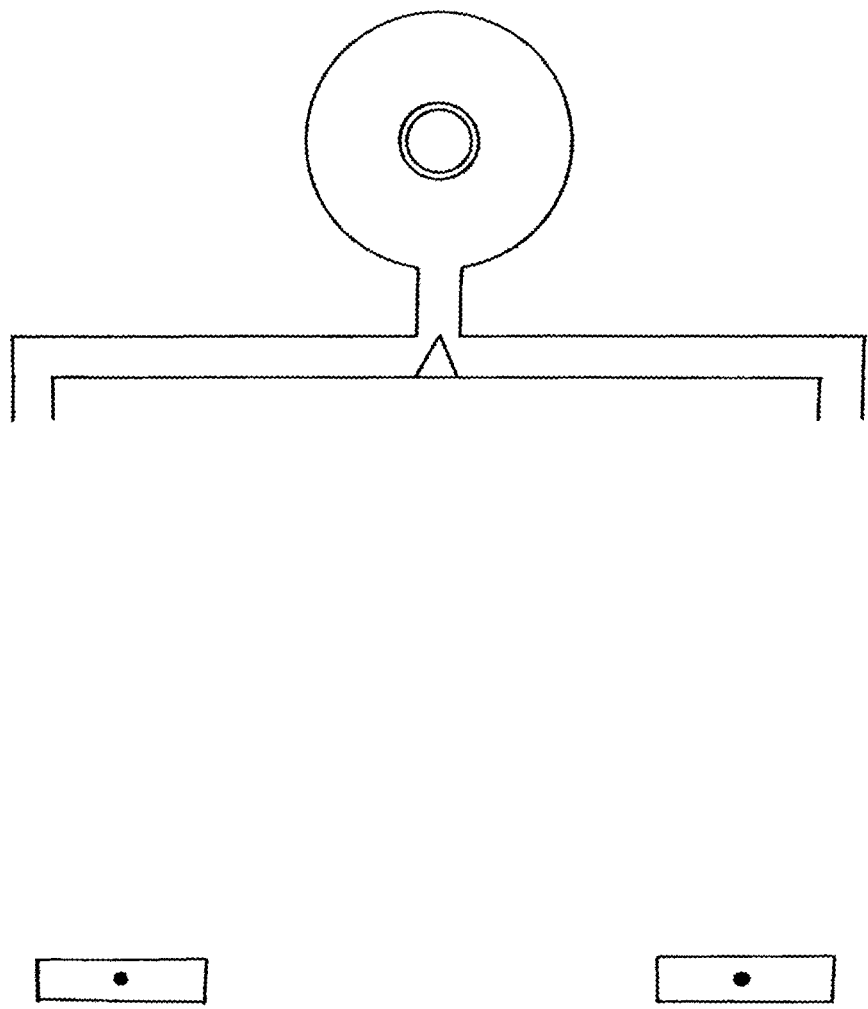
FIG. 3: View for the inside (almost half-deep cut) of Rakan's adjustable squint device—without threads connecting the two parts.

FIG. 3 shows the inside (almost half-deep cut) of Rakan's adjustable squint device without threads and it shows the two fixating wedges.

Figure 16:
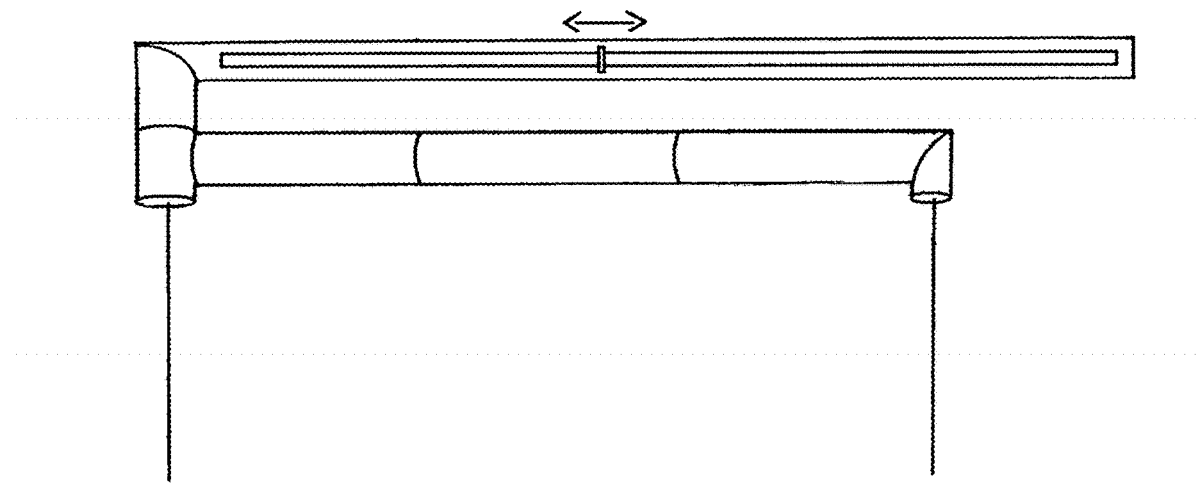
FIG. 16: Fixed insertion part of Rakan's adjustable squint device using straight adjuster—the arrows illustrate moving directions of the sliding piece.
Figure 17:
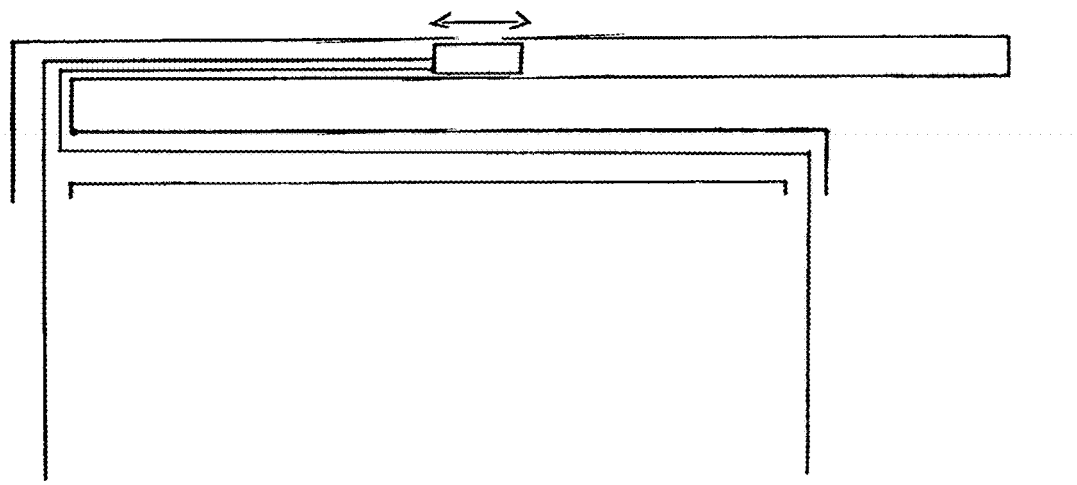
FIG. 17: View for the inside (almost half-deep cut) of Fixed insertion part of Rakan's adjustable squint device using straight adjuster—with threads (the arrows illustrate moving directions of the sliding piece).

Instead of using a rotatory or cylindrical adjustable piece we may use a sliding straight adjustable piece as shown in FIG. 16 and from inside FIG. 17, when we move the slide inside we determine the two threads length and the distance between the two parts of Rakan's adjustable squint device.

Figure 18:
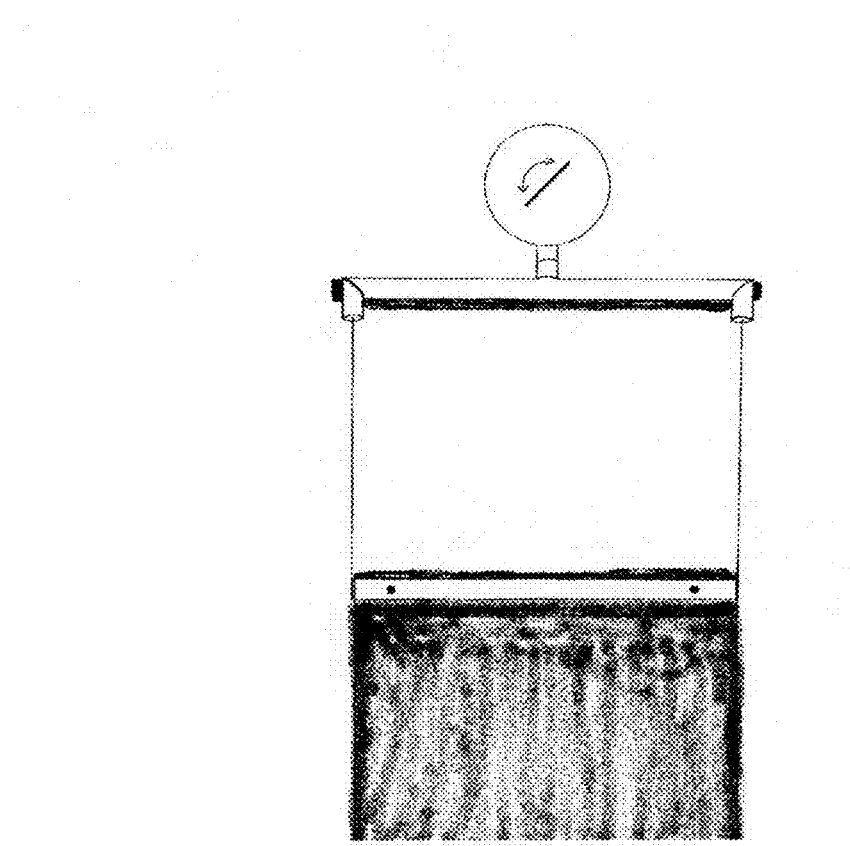
FIG. 18: Rakan's adjustable squint device implanted with the fixed part fixed over the muscle insertion and the movable part attached to the muscle/muscle tendon, the two parts are connected at both sides by two threads.

FIG. 18 shows Rakan's adjustable squint device implanted with the fixed part fixed over the muscle insertion and the movable part attached to the muscle/muscle tendon, and the two parts are connected at both sides by two threads, when the handle of the adjustable part of the fixed insertion part is rotated with the threads wrapping around the hollow shaft, the two threads length between the two parts of the device will be shortened so the movable muscle/muscle tendon part will become closer to the insertion, and when the handle of the adjustable part is rotated in the opposite direction, the movable part will become more far away, so by this we can adjust the magnitude of recession or resection when ever needed.

Figure 28:
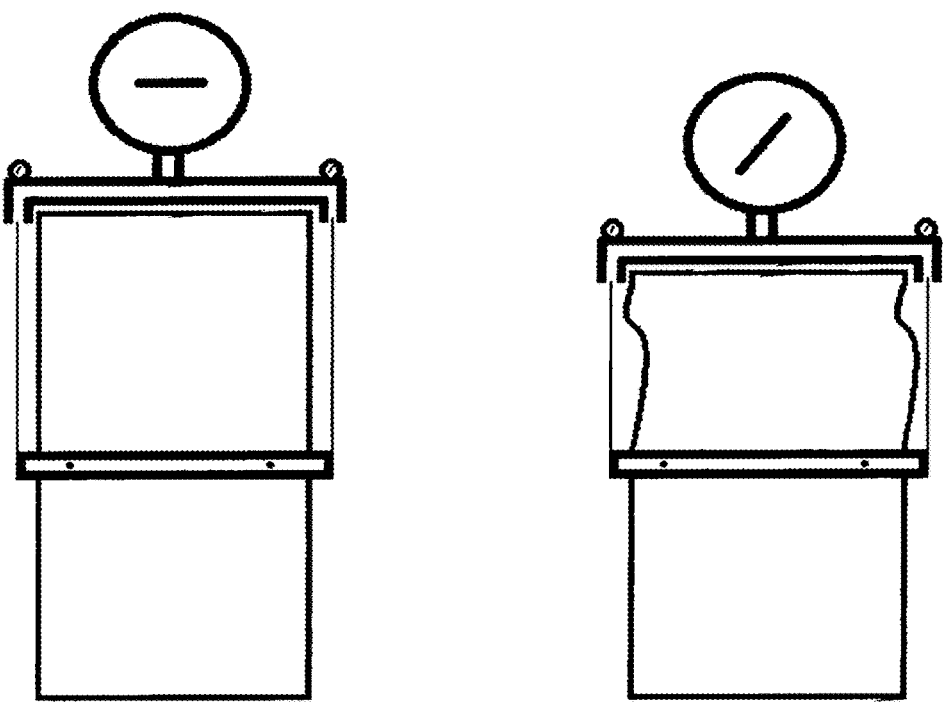
FIG. 28: Alternative to resection procedure.
Figure 29:
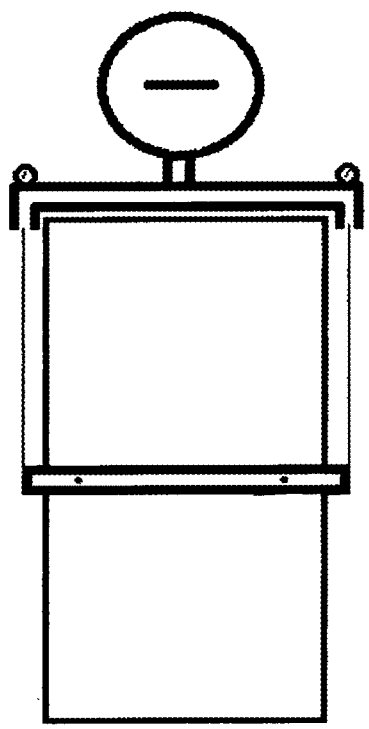
FIG. 29: This drawing shows the implantation of Rakan's adjustable squint device at the extra ocular muscle after exposure and dissection (the extra ocular muscle is represented as a rectangular).
Figure 30:
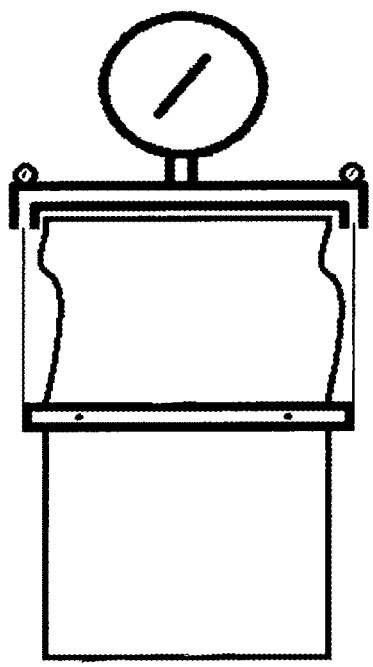
FIG. 30: This drawing shows the shortening of the extra ocular muscle after torsion of the rotatory piece of the adjustable part, so the threads' length is shortened between the two parts of the device, hence the muscle is shortened.

Alternative to resection procedure FIG. 28 is a new procedure in which we don't resect the muscle, instead of that we implant the fixed insertion part over the insertion using sclera screws or sutures and fixate the movable part on the muscle/muscle tendon in a place away from the insertion as shown in FIG. 29 then decrease the distance between the two parts by rotating the adjustable part as shown in FIG. 30, so by this we shorten the muscle without cutting or resecting it, and we may adjust the magnitude of the shortening as needed. In alternative to resection procedure we may use suturing without using Rakan's adjustable squint device; this would be achieved by fixating the suture far away from the insertion at both sides then connecting the sutures to the insertion, pull and shorten the muscle and tie the suture of the both sides together, so we shorten the muscle but do not resect it.

Figure 19:
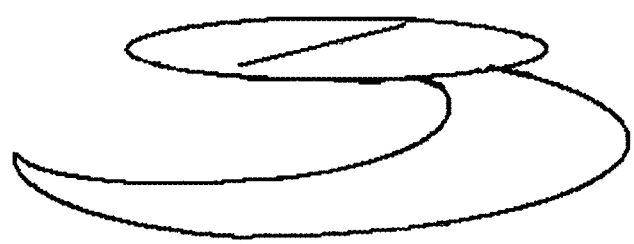
FIG. 19: Rakan's sclera screw (one screw thread).
Figure 20:
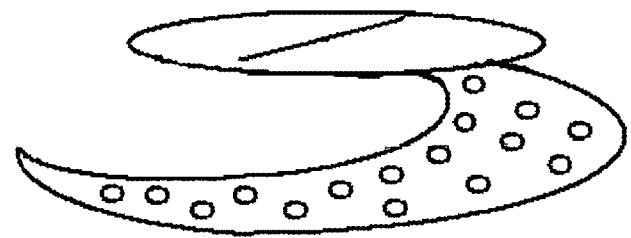
FIG. 20: Rakan's sclera screw (one screw thread)—screw thread is fenestrated.
Figure 21:
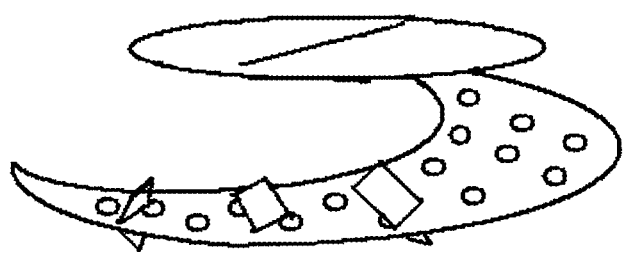
FIG. 21: Rakan's sclera screw (one screw thread)—screw thread is fenestrated and has a male buckle system (leaflets).
Figure 22:
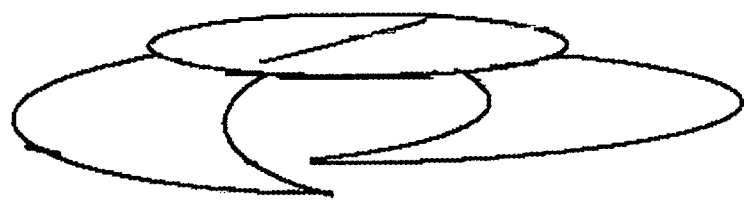
FIG. 22: Rakan's sclera screw (two screw threads_taper-point tips).
Figure 23:
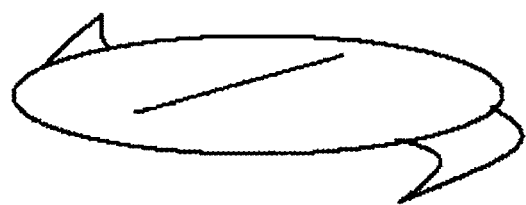
FIG. 23: Rakan's sclera screw (two screw threads/blades_taper-point tips).
Figure 24:
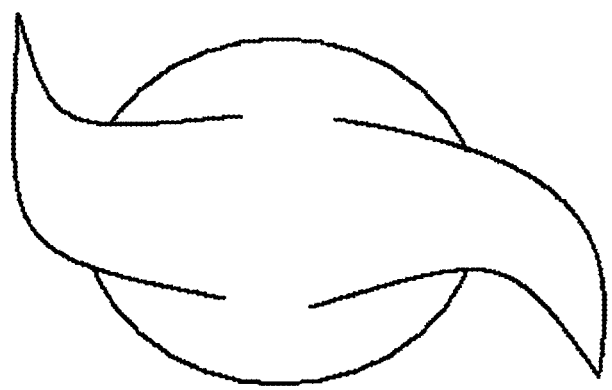
FIG. 24: Rakan's sclera screw (two screw threads/blades_taper-point tips)—below view.
Figure 25:
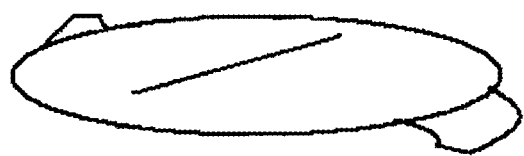
FIG. 25: Rakan's sclera screw (two screw threads_straight-cutting tips).
Figure 26:
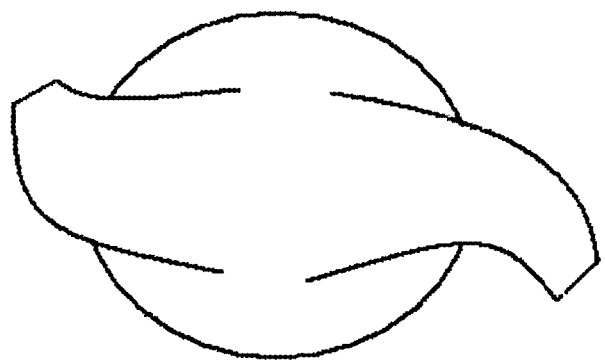
FIG. 26: Rakan's sclera screw (two screw threads_straight-cutting tips)—below view.
Figure 27:
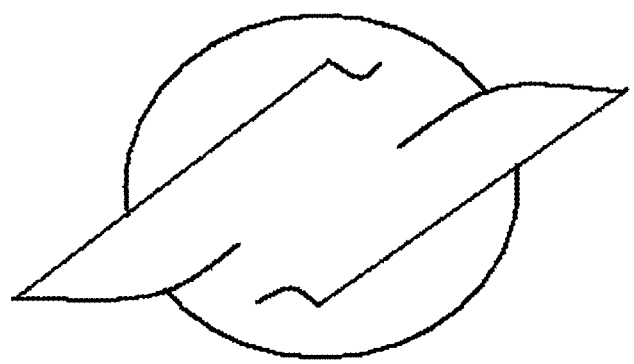
FIG. 27: Rakan's sclera screw (two screw threads_straight-cutting tips)—below view.

Rakan's sclera screws are screws that are lodged in the sclera without penetrating through the full thickness, sclera screws can be used instead of suturing in order to fixate any device implanted on the sclera. Rakan's sclera screws have many designs; with one screw thread as shown in FIG. 19 or with two screw threads as shown in FIG. 22/FIG. 23/FIG. 24/FIG. 27 or even with more than two screw threads. The screw thread could be fenestrated with tiny pores as shown in FIG. 20 (because theoretically this will give it more stability after the occurrence of fibrosis through the pores), or it could have a male buckle system—like leaflets as shown in FIG. 21 (which prevents backward rotation or spinning of the screw thread). Screw thread could have a taper-point tip as shown in FIG. 19/FIG. 20/FIG. 21/FIG. 22/FIG. 23/FIG. 24, or could have a straight-cutting tip as shown in FIG. 25/FIG. 26/FIG. 27.

The invention claimed is:

1. A method of shortening an extraocular muscle of the eye, the method comprising:
dissecting of conjunctiva and exposing an extraocular muscle;
implanting an adjustable squint device to the exposed extraocular muscle; and
approximating parts of the implanted adjustable squint device;
wherein the adjustable squint device comprises two parts:
a first part comprising:
(i) an adjustable portion having an outer fixed piece and an inner rotatory piece; said outer fixed piece is a hollow cylindrical-shaped container configured to receive the inner rotatory piece; said hollow cylindrical-shaped container including a central cylindrical shaft; said inner rotatory piece having a handle and a central hollow cylinder; said central cylindrical shaft placed inside said central hollow cylinder, and (ii) a tubule system portion with two attached apertures; said tubule system portion comprises four hollow tubules configured as two parallel tubules connected to both ends of a third elongated tubule, with a fourth tubule connected to center of the third elongated tubule in opposite direction to the two parallel tubule; said third elongated tubule having two attached apertures adjacent to the two parallel tubules; said fourth tubule connects the tubule system portion to the adjustable portion, and a second part comprising:

(i) a plate-shaped shaft with two apertures, and (ii) two wedge structures, each of said wedge structures comprises a plate-shaped base, a cylindrical shaft, and a hook-shaped tip;

wherein the first part and the second part of the adjustable squint device are connected with two threads, said threads connects both ends of the plate-shaped shaft of the second part, to the cylinder of the inner rotatory piece of the adjustable portion of the first part, through the tubule system portion of the first part, and configured as one thread at each side of the adjustable squint device;

wherein the method of implanting of the device comprises (i) implanting of the first part by: placing the third elongated tubule of the tubule system portion at the extraocular muscle insertion, with the two parallel tubules at both sides of the muscle insertion and in a direction toward the extraocular muscle; connecting the tubule system portion to sclera by using sclera screws lodged into the sclera through the apertures of the tubule system portion; wherein each sclera screw comprises: a head with a drive and two sharp curved blades, and (ii) implanting of the second part by: placing the plate-shaped shaft of the second part on the extraocular muscle; inserting the hook-shaped tip and the cylindrical shaft of the wedge structure through the extraocular muscle; fastening the hook-shaped tip of the wedge structure into the apertures in the plate-shaped shaft of the second part;

wherein approximating parts of the implanted adjustable squint device comprises wrapping said threads around the cylinder of the inner rotatory piece of the adjustable portion by rotating the handle of the inner rotatory piece;

wherein wrapping said threads approximates the second part toward the first part of the adjustable squint device causing shortening of the extraocular muscle of the eye, and wherein the extraocular muscle is shortened without cutting or resecting it.

* * * * *